United States Patent
Serlie

(10) Patent No.: US 10,956,411 B2
(45) Date of Patent: Mar. 23, 2021

(54) DOCUMENT MANAGEMENT SYSTEM FOR A MEDICAL TASK

(71) Applicant: KONINKLIJKE PHILIPS N.V., Eindhoven (NL)

(72) Inventor: Iwo Willem Oscar Serlie, Best (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 638 days.

(21) Appl. No.: 15/036,423

(22) PCT Filed: Nov. 20, 2014

(86) PCT No.: PCT/EP2014/075066
§ 371 (c)(1),
(2) Date: May 13, 2016

(87) PCT Pub. No.: WO2015/078754
PCT Pub. Date: Jun. 4, 2015

(65) Prior Publication Data
US 2016/0292363 A1    Oct. 6, 2016

(30) Foreign Application Priority Data

Nov. 29, 2013 (EP) ...................... 13195057

(51) Int. Cl.
*G16H 50/70* (2018.01)
*G16H 10/60* (2018.01)
(Continued)

(52) U.S. Cl.
CPC ............ *G06F 16/245* (2019.01); *G06F 16/93* (2019.01); *G16H 10/60* (2018.01); *G16H 50/70* (2018.01)

(58) Field of Classification Search
None
See application file for complete search history.

(56) References Cited

U.S. PATENT DOCUMENTS 7,284,191 B2 * 10/2007 Grefenstette ........... G06F 16/30
                                                             715/230
9,842,113 B1 * 12/2017 Sorvillo ................ G06F 16/156
(Continued)

OTHER PUBLICATIONS

Koch, O. "Process-based and context-sensitive information supply in medical care". Context—Conference on Modeling and Using Context, Publication 307, 2007.
(Continued)

*Primary Examiner* — Michael Tomaszewski
*Assistant Examiner* — Jay M. Patel

(57) ABSTRACT

A document requesting unit (150) and a document suggestion unit is provided. The document requesting unit is configured for retrieving documents to assist a first user in a first clinical task on patient data of a first patient, the document requesting unit (150) comprising a context builder (157) configured to determine a first context (142) based on a description of the first clinical task and/or the patient data of the first patient, a database unit (152) configured to retrieve a document (122) selected by the user from an electronic document database (120), and a tagging unit (156) configured to tag the selected document (122) with the first context to enable a document suggestion unit (250) to suggest the selected document (122) during a second clinical task on patient data of a second patient. The document suggestion unit (250) is configured for suggesting a document to the user to assist the user in the second clinical task on patient data of the second patient, the document suggestion unit (250) comprising a context builder (157) configured to determine a second context (242) based on the second clinical task and/or the patient data of the second patient, a matching unit (254) configured to determine a match valuation between the second context and a tagged context of a candidate document (222) in the document
(Continued)

database (120), and to suggest the candidate document to the user if the match valuation is high according to a suggestion function.

15 Claims, 8 Drawing Sheets

(51) Int. Cl.
*G06F 16/245* (2019.01)
*G06F 16/93* (2019.01)

(56) References Cited

U.S. PATENT DOCUMENTS

| | | | | |
|---|---|---|---|---|
| 10,130,872 | B2* | 11/2018 | Buhr | A63F 13/30 |
| 2003/0083914 | A1* | 5/2003 | Marvin, III | G06Q 40/04 |
| | | | | 705/37 |
| 2006/0024654 | A1* | 2/2006 | Goodkovsky | G09B 7/02 |
| | | | | 434/350 |
| 2006/0129538 | A1* | 6/2006 | Baader | G06F 16/951 |
| 2006/0136270 | A1* | 6/2006 | Morgan | G06Q 50/24 |
| | | | | 705/3 |
| 2007/0112845 | A1* | 5/2007 | Gilmour | G06Q 30/0201 |
| 2008/0201280 | A1* | 8/2008 | Martin | G06Q 50/24 |
| | | | | 706/12 |
| 2008/0275731 | A1* | 11/2008 | Rao | G06Q 50/24 |
| | | | | 705/3 |
| 2008/0313000 | A1* | 12/2008 | Degeratu | G06Q 10/06 |
| | | | | 705/319 |
| 2009/0132653 | A1* | 5/2009 | Niazi | G06Q 10/00 |
| | | | | 709/204 |
| 2009/0307162 | A1* | 12/2009 | Bui | G06N 5/022 |
| | | | | 706/12 |
| 2010/0159438 | A1* | 6/2010 | German | G06F 16/24573 |
| | | | | 434/433 |
| 2010/0169983 | A1* | 7/2010 | Horr | G06F 21/6218 |
| | | | | 726/28 |
| 2011/0054946 | A1* | 3/2011 | Coulter | G16H 30/20 |
| | | | | 705/3 |
| 2011/0119075 | A1* | 5/2011 | Dhoble | G06Q 50/22 |
| | | | | 705/2 |
| 2011/0236870 | A1* | 9/2011 | Chinosornvatana | G09B 7/08 |
| | | | | 434/322 |
| 2011/0288877 | A1* | 11/2011 | Ofek | G06Q 10/10 |
| | | | | 705/2 |
| 2012/0060216 | A1* | 3/2012 | Chaudhri | G16H 10/60 |
| | | | | 726/21 |
| 2012/0191793 | A1* | 7/2012 | Jakobovits | G06F 19/321 |
| | | | | 709/206 |
| 2012/0215560 | A1* | 8/2012 | Ofek | G16H 10/00 |
| | | | | 705/3 |
| 2012/0239671 | A1* | 9/2012 | Chaudhri | G16H 20/00 |
| | | | | 707/756 |
| 2012/0303501 | A1* | 11/2012 | Chung | G06Q 40/08 |
| | | | | 705/35 |
| 2013/0290323 | A1* | 10/2013 | Saib | G06F 16/113 |
| | | | | 707/728 |
| 2014/0025732 | A1* | 1/2014 | Lin | A63F 13/795 |
| | | | | 709/204 |
| 2014/0172996 | A1* | 6/2014 | Deeter | H04L 51/14 |
| | | | | 709/206 |
| 2014/0350961 | A1* | 11/2014 | Csurka | G16H 10/60 |
| | | | | 705/3 |
| 2015/0032464 | A1* | 1/2015 | Vesto | G06F 19/3418 |
| | | | | 705/2 |
| 2016/0378919 | A1* | 12/2016 | McNutt | G06Q 50/24 |
| | | | | 705/3 |

OTHER PUBLICATIONS

Martins, D.S. et al. "Implicit relevance feedback for context aware information retrieval in UbiLearning environments", Applied Computing, 2009, pp. 659-663.

* cited by examiner

DOCUMENT MANAGEMENT SYSTEM FOR A MEDICAL TASK

CROSS-REFERENCE TO PRIOR APPLICATIONS

This application is the U.S. National Phase application under 35 U.S.C. § 371 of International Application No. PCT/EP2014/075066, filed on Nov. 20, 2014, which claims the benefit of European Patent Application No. 13195057.8, filed on Nov. 29, 2013. These applications are hereby incorporated by reference herein.

FIELD OF THE INVENTION

The invention relates to a document management system comprising a document requesting unit for retrieving documents to assist a first user in a first clinical task on patient data of a first patient, the document requesting unit comprising a database unit configured to retrieve a document selected by the user from an electronic document database. The invention further relates to a method for document management, and a corresponding computer program.

BACKGROUND

Significant amounts of information have to be consulted by clinicians to make informed decisions: patient information (e.g. observation and history) as well as reference information (e.g. norms). Furthermore, it is complex to work according to the latest medical evidence.

For example, radiologists or referring physicians may need to consult such most up-to-date external knowledge sources as reference materials, to make informed decisions on, image interpretations, lesion recognitions, treatment suggestions, and the like. Despite the aforementioned information needs, the time available to make a decision is limited.

In the paper "Process-based and context-sensitive information supply in medical care" by Oliver Koch, this situation is also acknowledged. According to Koch, physicians usually get access to information and knowledge by using medical information systems (clinical information systems, laboratory systems, medical practice management software etc.), local databases, e-resources or traditional print media.

Koch proposes a context-sensitive supply of additional information at the physicians' workplace, via a so-called 'Infobutton'. The infobutton automatically generates and sends queries to electronic health information resources (e-resources) using patient data extracted from the electronic medical record and context information that is captured from the interaction between a clinical user and a clinical information system. The information request includes particular context information. These are basically elementary patient attributes (age, gender), the physicians' actual activity (e.g. patient information review) and main search concept (e.g., lab parameters or diagnosis) and including additional qualifying attributes and information about the physicians' role and language.

The automatic querying of documents based on a current context has proven not to be entirely satisfactory for clinical users. Inevitably, some documents will be suggested even though they are irrelevant. In that case the information overflow is only aggravated rather than alleviated. Furthermore, documents might not be suggested even though they are relevant.

As will be discussed below, other points of the Koch's proposal may also be improved upon.

SUMMARY OF THE INVENTION

It would be advantageous to have an improved document management system that improves the workflow of a user working on a clinical task. It would further be advantageous to have an improved document management system that alleviates the other shortcomings noted herein.

A document management system is provided that comprises a document requesting unit for retrieving documents to assist a first user in a first clinical task on a first patient. The document requesting unit comprises a context builder, a database unit and a tagging unit. The context builder is configured to determine a first context based on a description of the first clinical task and/or the patient data of the first patient. The database unit is configured to retrieve a document selected by the first user from an electronic document database. The tagging unit is configured to tag the selected document with the first context to enable a document suggestion unit to suggest the selected document during a second clinical task on patient data of a second patient by a second user.

By tagging documents that were actually retrieved or selected by a user when working on a clinical task for a patient, the system learns which documents were actually relevant in a given clinical context. This in turns allows a document suggestion unit to suggest documents that are proven to be important to at least some users, instead of suggesting documents that seem important based on a comparison of context, popularity statistics and document data.

A document suggestion unit is provided for suggesting a document to the second user to assist the user in the second clinical task on patient data of the second patient. The document suggestion unit comprises a context builder and a matching unit. The task context builder is configured to determine a second context based on the second clinical task and/or the patient data of the second patient. The matching unit is configured to determine a match valuation between the second context and a tagged context of a candidate document in the document database, and to suggest the candidate document to the user if the match valuation is high according to a suggestion function.

In this way documents are suggested that are useful in a given context. Moreover, if it turns out that another document is needed, the system will learn through tagging. If the same context appears later, the system has an improved suggestion. The suggestions of the known system are static and do no change over time. The suggestions of the known system are based on the current context only in contrast to the proposed system where suggestions are based on the current context as well as prior contexts grouped with specific documents.

The known system does not learn which materials support a particular task for a particular patient case for a specific person in a care team. Furthermore, the known system does not allow users and colleagues to benefit from experience in a care-team. The first and second user may be the same or different. A tag created by a first user for a document may be used to suggest that document later to a second user, different from the first user. In an embodiment, the first or second context is based additionally on identity information of the user, and/or a role of the user. The background of the user is an important hint on the significance of the document. For example, a document that is consulted by an oncologist is more likely to be relevant to other oncologists.

In an embodiment the context comprises information on user, task and patient. There is considerable synergy in having all three components. The identity information may be obtained from a user profile. In the latter case, the user profile of the first user is used to build the tag; the profile of the second user is used to build the second context.

The context may also include the seniority of the user. The match valuation may be configured so that a high seniority in the second context does not match a tag with a low seniority, but a low seniority in the second context does match a tag with a high seniority. High and low seniority may be defined by a corresponding threshold, e.g., High seniority is more than 5 years experience and low seniority is less than 5 years experience. High seniority may also be defined using different criteria, for example having done more than a predetermined number of clinical tasks, e.g., using the document management system, or having read more than a number of specific patient studies.

In an embodiment the matching unit is configured with a local mode. In the local mode the matching unit determines a match valuation between the second context and a tagged context of a candidate document in the document database only if the tagged context was made by the second user. A suggested document according to the local mode may be suggested to the user, e.g., visually distinctive from a document suggested by taking tags into account suggested by different users.

In an embodiment, the document suggestion unit determines a document suggestion based on a tag created by the second user, and In an embodiment, the system is configured for multiple users to tag documents in the document database, the suggestion unit may be configured to match tags that were created by the same or a different user.

An aspect of the invention concerns a workstation or imaging apparatus comprising the document management system. The patient data may include a patient study comprising multi-dimensional image data, e.g. to two-dimensional (2D), three-dimensional (3D) or four-dimensional (4D) images, acquired by various acquisition modalities such as, but not limited to, standard X-ray Imaging, Computed Tomography (CT), Magnetic Resonance Imaging (MRI), Ultrasound (US), Positron Emission Tomography (PET), Single Photon Emission Computed Tomography (SPECT), and Nuclear Medicine (NM).

For example, the context builder may use available patient context that may have been obtained from a patient imaging study. For example, oncologists with the task of suggesting a therapy on the basis of the report of a radiologist, but subsidiary also the original patient study data. The second user may be an oncologist using information of a radiologist.

Not only imaging data may be used, for example, the context builder may use palpation data, visual observation, etc.

The task may even be to select multiple therapy options for later discussion with the patient or within a care team. Through the document management system the whole care team receives improved document suggestions.

The document management system including the document requesting unit and document suggestion unit are electronic devices.

A method according to the invention may be implemented on a computer as a computer implemented method, or in dedicated hardware, or in a combination of both. Executable code for a method according to the invention may be stored on a computer program product. Examples of computer program products include memory devices, optical storage devices, integrated circuits, servers, online software, etc. Preferably, the computer program product comprises non-transitory program code means stored on a computer readable medium for performing a method according to the invention when said program product is executed on a computer.

In a preferred embodiment, the computer program comprises computer program code means adapted to perform all the steps of a method according to the invention when the computer program is run on a computer. Preferably, the computer program is embodied on a computer readable medium.

BRIEF DESCRIPTION OF THE DRAWINGS

These and other aspects of the invention are apparent from and will be elucidated with reference to the embodiments described hereinafter. In the drawings.

Figure 1:
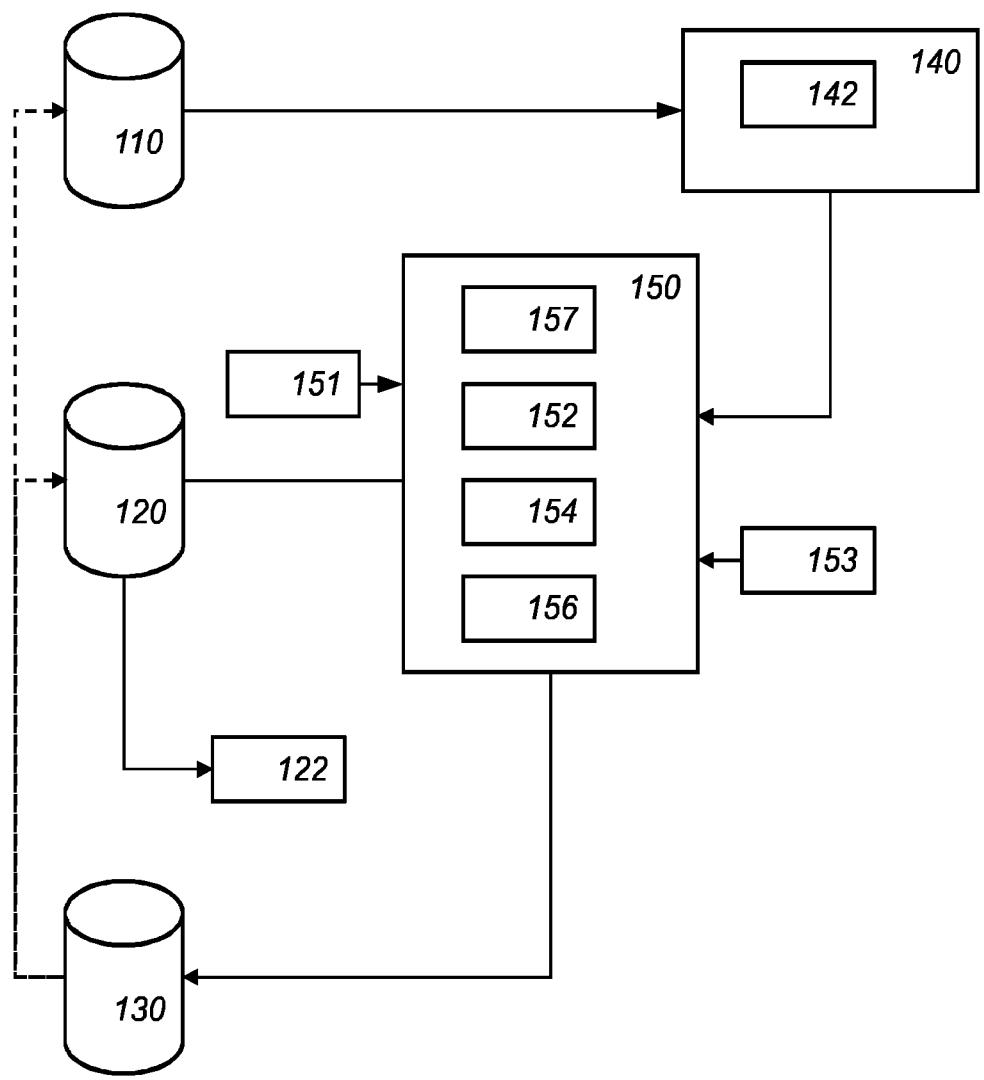
FIG. 1 is schematic block diagram of a document management system 100 comprising a document requesting unit 150.

It should be noted that items which have the same reference numbers in different Figures, have the same structural features and the same functions, or are the same signals. Where the function and/or structure of such an item have been explained, there is no necessity for repeated explanation thereof in the detailed description.

LIST OF REFERENCE NUMERALS IN FIGS.
1-3

100, 200, 300, 301 document management system
110 a patient database
120 a document database
122 a selected document
130 a tag database
140 a temporary context storage
142 a first context
150 a document requesting unit
151 a query
152 a database unit
153 a selection
154 a sorting unit
156 a tagging unit
157 a context builder
210 a filter database 222 a candidate document
242 a second context
250 a document suggestion unit
252 an context filter
254 a matching unit
310 a server
320 multiple users
322, 324 a user
330 common interface

DETAILED DESCRIPTION OF EMBODIMENTS

While this invention is susceptible of embodiment in many different forms, there is shown in the drawings and will herein be described in detail one or more specific embodiments, with the understanding that the present disclosure is to be considered as exemplary of the principles of the invention and not intended to limit the invention to the specific embodiments shown and described.

Figure 2:
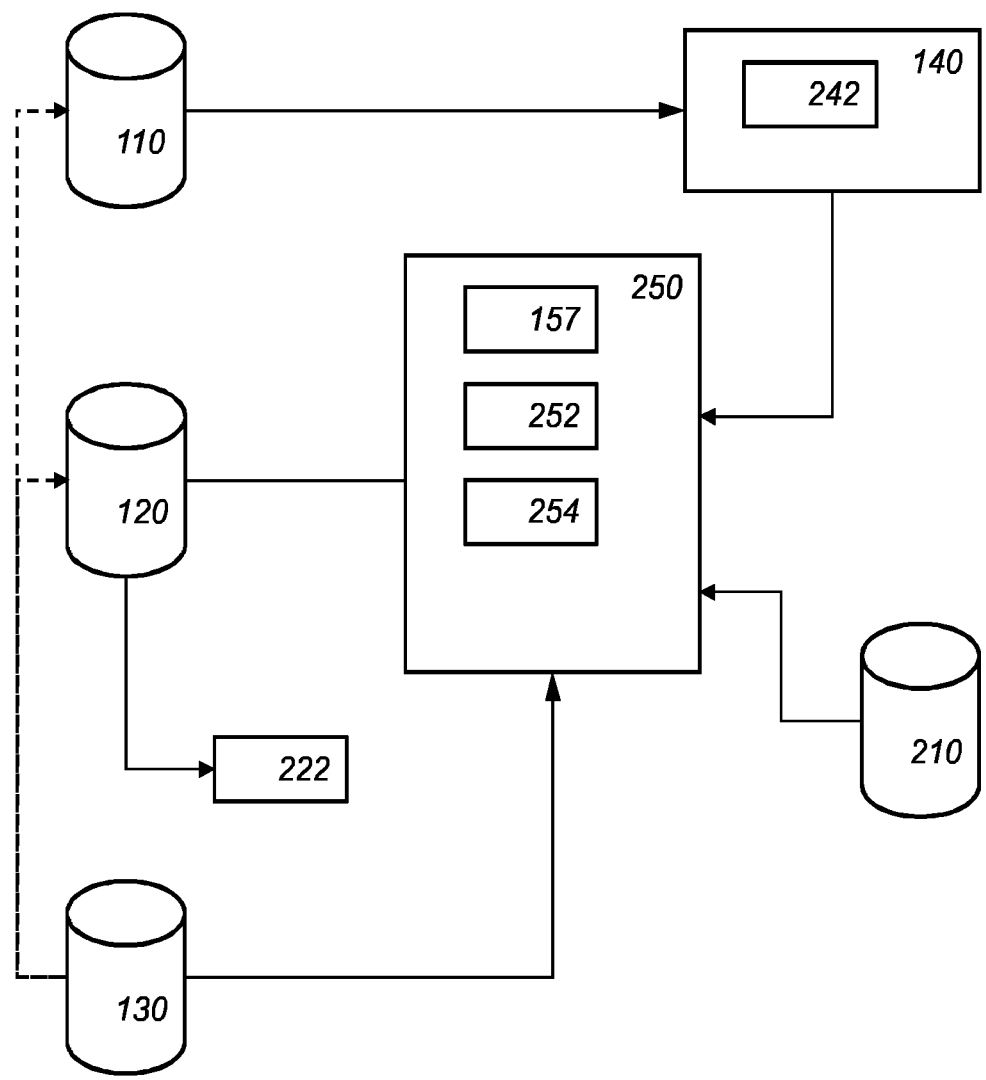
FIG. 2 is schematic block diagram of a document management system 200 comprising a document suggestion unit 250.

FIG. 1 is schematic block diagram of a document management system 100 comprising a document requesting unit 150. The document requesting unit 150 is suited to be used together with a document suggestion unit 250. A document management system 200 is shown in FIG. 2 which comprises such a document suggestion unit 250. Document requesting unit 150 comprises a tagging unit 156 configured to tag selected documents with a context to enable the document suggestion unit 250 to suggest documents during a second clinical task on patient data of a second patient.

FIG. 1 shows a document management system 100 comprising a document requesting unit 150. Document requesting unit 150 is configured for retrieving documents to assist a user in a first clinical task on patient data of a first patient.

The system is suited to a user who is executing a specific clinical task in the context of a patient study. Typically, the user is a medical professional who needs to interpret patient data. The patient data may be interpreted in isolation or in combination with other sources of data, e.g., direct observation of the patient. The system may be used without the patient being present. For example, the user may be a radiologist or an oncologist.

Document requesting unit 150 comprises a database unit 152.

The database unit 152 is configured to retrieve a document 122 selected by the user from an electronic document database 120. Document database 120 may be comprised in document requesting unit 150. For example, document requesting unit 150 and document database 120 may run on the same server or computer system. The connection between document requesting unit 150 and document database 120 may be over a computer network, e.g., a LAN or the internet. Document requesting unit 150 may use a so-called API to access document database 120.

However, in a typical implementation document database 120 is implemented on a different resource than document requesting unit 150. Document database 120 may be a collection of a hospital's trusted sources, i.e., a collection of documents that the hospital wants its professionals to work with. Document database 120 may be obtained as a subscription service from a document provider. Document database 120 may be comprised of several sub-databases. For example, document database 120 may contain one or more of: Scientific literature, Guidelines, Clinical trials, Hospital trusted sources, and User's trusted sources.

Note that part or all of the documents in document database 120 may be non-machine readable, i.e., not machine-interpretable. In an embodiment, document database 120 comprises one or more image-only documents, the tagging unit being configured to tag an image-only document. The latter is suitable for, e.g., scanned handwritten notes, or image collections, such as image atlases. The known system cannot suggest image-only documents as it cannot compare a context with an image only document.

Access to document database 120 may be implemented in several ways. For example, document requesting unit 150 may offer a file browser. Through the file browser the user can select the file he requests. For example, document requesting unit 150 may show a list of document names or a document tree, say organized by topic, from which a document may be selected.

The documents may be electronic documents that are stored locally. They may also include electronic references to externally stored documents, e.g., URL's. The documents may have such file formats as: ppt, pdf, bmp, and the like. The documents may include a URL to a domain in which the documents are stored.

Document requesting unit 150 is well suited for use with a query based document request system. This optional feature is shown in FIG. 1. The database unit 152 may be configured to receive a query 151 from the user. Database unit 152 may be configured to determine responding documents from document database 120. For example, database unit 152 may generate a command for a query API of document database 120 corresponding to query 151. The responding documents, or part thereof, are shown to the user, say as a list of document names, possibly together with a content indication. Database unit 152 is configured to receive a selection 153 from the user for one of the responding documents; in this case selected document 122.

Document requesting unit 150 is configured to make the selected document electronically available to the user, typically by showing it on an electronic display. Document requesting unit 150 could also provide an electronic reference to selected document 122, say a so-called link, say a URL, or make the selected document 122 available for download, have the document printed, etc.

If database unit 152 is configured with a query based search system, then database unit 152 may be configured to search in multiple electronic databases. For example, one may be closed database, say from a medical document supplier, comprising comparatively few documents, say less than 1000, or less than 10000. For example, one may also use an on-line search facility, which may contain much more, but less trusted documents. Unit 152 may be configured with a different query algorithm per database, using a different API, and possibly a different query generation algorithm. The received results may then be combined by unit 152 into a single list. Regardless of the source of a document, a user can tag it, since the tags are stored locally in database 130.

Document requesting unit 150 further comprises a context builder 157, and a tagging unit 156.

Context builder 157 is configured to determine a first context 142 based on a description of the first clinical task and/or the patient data of the first patient. Informally, the context builder 157 builds an electronic representation of the context in which selected document 122 was requested. When a similar context later arises, a document suggestion unit can suggest document 122.

A patient context, including context 142, may contain any one of the following two components: 1) information relating to the current patient, 2) information regarding the current task the user performs on the patient data and/or the role of the user. Details of these two options are explained below. Miscellaneous other information may also be included in the context, e.g., the date selected document 122 was accessed.

Information Relating to the Current Patient

The patient information may include medically relevant prior medial information. These might be obtained from a medical image and information management system, e.g. a picture archiving and communication system (PACS), such as the currently available IntelliSpace PACS. For example, document requesting unit 150 may be connected to an electronic patient database 110 to receive patient data. For example, document requesting unit 150 may request data using an API of patient database 110. The patient information may include information describing the physical condition of the patient, e.g., age, gender, existing conditions, lifestyle information, e.g., smoking or non-smoking Patient database 110 may be part of a hospital information system.

Including this information in the context later allows retrieval of selected document 122 when a similar patient study is performed. For example, a document relevant for this breast cancer patient may also be relevant in relation to a future breast cancer patient. For example, a document relevant for a senior female patient may not be relevant for a teenage boy.

The patient data may also include formal data including: patient name, medical record number (MRN), etc. This allows suggestion of selected document 122 when a new task needs to be performed on this patient's data in the future. This feature may also be used in experience sharing, further discussed below.

Context builder 157 may be configured to make a literal copy of all or part of the patient data from patient database 110 to the first context 142. In an embodiment, the task context builder 157 is configured to include a reference to the patient data in an electronic patient database 110. The reference may be used instead of the literal copy; this saves space. The reference may be used in addition to the literal copy; this ensures that up-to-date information is available when the tag of selected document 122 is accessed in future.

Information Regarding the Current Task the User Performs on the Patient Data and/or the Role of the User The patient data may include information related to the current task: task description, body part, etc. Document requesting unit 150 may obtain this information from a hospital information system. The information may also entered by the user or an assistant of the user. Typically, the task description is selected from a list of tasks. For example, the task may be to define a skeletal age. The task may be encoded, say with an integer value. The task may be in natural language.

In addition to the description of the task, the context may also include information regarding the user of selected document 122, for example, identity information of the user. The identity information may be represented by a log-in name that the user used to gain access to document requesting unit 150. In addition or alternatively, the context may include the role of the user, e.g. radiologist or oncologist. The role may be obtained from a role data base (not separately shown) that maps names to roles.

In an embodiment, the context also includes the seniority of the user. This information is particularly advantageous, as it can later be used to filter suggestions. Documents that are relevant for users with little experience may be distracting for users with high experience, even if they share the same role.

User information may be obtained via user profiles.

As an example: In a first embodiment, the context comprises at least a task description. In a second embodiment, the context comprises at least a task description and medical patient information. In a third embodiment, the context comprises at least a task description, medical patient information and user information. Experiments have shown that the combination of patient data and task data is already well suited for suggesting relevant documents.

Document requesting unit 150 may comprise temporary context storage 140 for storing first context 142. Document requesting unit 150 may be configured start generation of first context 142 immediately upon selection of a specific patient and task. At the moment a document is selected, it can be tagged using the information already present in temporary context storage 140. Temporary context storage 140 may be implemented using a number of storage technologies, e.g. volatile or non-volatile memory, magnetic storage and the like.

Document requesting unit 150 comprises a tagging unit 156 configured to tag the selected document 122 with the first context to enable a document suggestion unit 250 to suggest the selected document 122 during a second clinical task on patient data of a second patient.

Tagging unit 156 may also tag document 122 with the parts of the documents that were visited, e.g., page, or section. This information may be used when suggesting the document, to also suggest a particular page or section. This is especially advantageous for longer documents, and/or documents that cover multiple topics.

In an embodiment, document management system 100 comprises an electronic tag database 130, wherein the tagging unit 156 is configured to tag the selected document 122 by recording in the tag database 130 the first context together with a reference to the selected document 122 in the document database 120. Storing tags in a separate database avoids the need to modify document database 120; this is suited for external databases.

Moreover database 130 allows tagging even if system 100 has only 'read'-access to the documents, but not 'write'-access.

Document requesting unit 150 may comprise an optional sorting unit 154 configured to sort documents which can be requested by the user according to suitability, e.g. clinical relevancy. The sorting unit may be used in combination with a file browser. Selection 153 is especially suited in combination with a query based request system. For example, the database unit 152 may be configured to receive a query 151 from the user. Database unit 152 may be configured to determine responding documents from document database 120. Before showing a list of responding documents, the list may be sorted by selection 153. Suitability of a particular document may be determined by matching the particular document with the first context 142. The matching between two documents, or between a context and a document, may be defined using a document distance function. The distance function may be based on a bag of word model, e.g., the cosine distance of two documents. The distance function may also be based on correlation.

Suitability of a particular document may also be determined by matching a tag of the particular document with the first context 142. Comparing a tag and a document may be done in the same way as comparing two documents. In case the tag is structured also other ways may be used, for example, one may search if a keyword or the like of the tag is present in the document to determine a match.

Suitability is first determined by matching a tag of the particular document with the first context 142. If not tag is available, or as a subsidiary criterion, then suitability may be determined by matching the particular document with the first context 142.

FIG. 2 is schematic block diagram of a document management system 200 comprising a document suggestion unit 250. Document suggestion unit 250 is configured for suggesting a document to the user to assist the user in the second clinical task on patient data of the second patient. Typically system 200 will also contain one or more devices 150. The devices 150 provide documents in document database 120 with tags. Note that the user that uses document suggestion unit 250 need not be the same user or users that used devices 150 and created tags. Not all document in document database 120 need to have tags, some may have tags, whereas some do not, or not yet.

Document suggestion unit 250 comprises a context builder 157 and a matching unit 254.

Context builder 157 in document suggestion unit 250 may be the same as context builder 157 in document requesting unit 150. In fact, if document requesting unit 150 and document suggestion unit 250 are embodied in a single device, as is well possible, then document requesting unit 150 and document suggestion unit 250 may share the same context builder 157. Context builder 157 of document suggestion unit 250 is configured to determine a second context 242 based on the second clinical task and/or the patient data of the second patient. The second patient is typically different from the first patient; however, it is possible to use the system on the same patient twice for different clinical tasks. In the latter case, the first and second patients are the same.

For example, like document requesting unit 150, document suggestion unit 250 may comprise a temporary context storage 140. Context builder 157 may store the second context 242 in the temporary context storage 140. Document suggestion unit 250 may be configured to generate second context 242 as soon as a patient and/or task has been selected. Interestingly, if document requesting unit 150 and document suggestion unit 250 are combined in a single device, a context may be created in temporary context storage 140. If a document is requested this context is available for tagging, and otherwise this context is available for document suggestion.

All or part of a context, including contexts 142 and 242, tags and patient data may be in accordance with a data exchange standards for medical environments. The data exchange standards may use a structured data language such as XML or ASN.1 For example; one may use HL7, which is an international standard for the exchange of data between computer systems in the health sector.

Document suggestion unit 250 comprises a matching unit 254 configured to determine a match valuation between the second context and a tagged context of a candidate document 222 in the document database 120, and to suggest the candidate document to the user if the match valuation is high according to a suggestion function.

A match valuation may be generated in the same way that sorting unit 154 compares a tag and a context or compares a context and a document. In particular, tags may be compared without taking their structure into account. However, if the tags are structured a more structured comparison is possible, for example, tags may be containing fields, and corresponding fields in the tags may be compared with each other. The matching unit 254 may be configured to correlate the second context with a tagged context of a candidate document 222 to obtain the match valuation.

Matching tags and context may also be done using a concept list, also referred to as a dictionary. The matching unit 254 comprises a concept list and is configured to map at least part of the second context to one or more concepts of the concept list and to determine a correlation between the one or more concepts and a tag of the candidate document to obtain the match valuation. Also words in the tag may be mapped to the concept list; this could also have been done when the tag was created.

The concept list may use a structured ontology, i.e., a formal representation of domain knowledge, such as 'RadLex'. Mapping to a concept list causes a semantic normalization: using structured knowledge sources improves the access to unstructured data. Also normalization results in language independence.

Experiments have shown that good results are obtained if matching unit 254 first performs two matchings, one using the concept list, and one without it, e.g., using natural language comparison. The two match valuations are then combined, say averaged, into a final match valuation.

Below a particular embodiment of matching unit 254 is given. This matching unit 254 arranged for matching (1) user, (2) task and (3) patient context information resulting in a combined match valuation. For example, consider the user match valuation: it may be 1 if user information exactly matches, that the same user is doing the second task as the first task, and it will be 0 if it does not match and it will be 0.5 if only the user's role and user's specialty match.

Furthermore, consider the task context: it may be 1 if the user is performing the same task and 0 if not performing the same task.

In addition, consider the patient match valuation. It may be 1 if there is an exact match between all properties. It may be 0 in case there is no match between any of the properties. It will be 0.5 if one of the patient characteristics partially matches. For example the body parts for two patient studies are not identical, but the parts share the same body region (e.g. finger and hand are both part of an upper extremity). Finally, the user, task and patient context are multiplied. In case a document is tagged with multiple user, task and patient contexts, the most relevant, resulting in the best match, will be selected. Other matching algorithms may be based on this information.

Context, whether in the form of a tag or in temporary context storage 140 may be structured data, say XML or ASN.1. For example, context may contain fields for 1) user name and role, 2) task and body part and 3) patient data, e.g., gender, and age.

The suggestion function may be arranged to suggest a document if the match valuation is above a suggestion threshold. Say, in the example above a document may be suggested if the match valuation is at least 0.5. The suggestion function may also show the one or more of the highest ranking documents.

Matching unit 254 may be configured to match second context 242 with multiple documents in document database 120 that are tagged, preferably, with all documents in document database 120 that are tagged. The suggestion function may be configured to suggest a suggestion number of document. The suggestion number may be 2 or 3, or higher.

Document suggestion unit 250 may be configured with a user interface subsystem for displaying a summary of the result set of documents (e.g. names of documents), e.g., containing hyperlinks to the actual documents. The user interface subsystem may be configured to highlight part of the suggested documents that relates to the context that resulted in the best match. Other matches might be highlighted using a different less prominent way (e.g. via a background color). For example, Document suggestion unit 250 may be configured to sort according to the match evaluation.

If the tag contains information on the parts of the documents that were visited, e.g., page, or section, the unit 250 may show this part of the document or part thereof.

If the tag contains information on the parts of the documents that were visited, e.g., then if the suggested document is selected for viewing, the viewer may open the document on the indicated part, e.g., page or section.

Document suggestion unit 250 may comprise a context filter 252, the context filter selecting part of the information from the second context 242 according to a filter associated with the user and/or second task. The matching unit 254 being configured to determine a match valuation between the selected part of the second context and a tagged context of a candidate document 222 in the document database 120. For example, the context filter may select only task information if the task is to define a skeletal age, as other information is likely not relevant to this task. However, if the task is classification of an image for oncology, the context filter may include task, gender and role. In this way document are filtered out that were suggested to classify images for a cardiology. Preferably, the filter is associated with the user and second task.

Including more information in tags and context 242 typically improves the quality of suggested documents, since the context in which a document was previously used and the context in which it is suggested are more closely related. On the other hand including more information reduces the number of suggested documents, because it will be rare that a close enough match between a first context 142 and a second context 242 occurs. Filtering alleviates this problem; it allows including more information in context and tags, thus improving the quality of matches. At the same time, because information which is currently irrelevant is filtered out, it is avoided that relevant document remain uncongested.

In addition to the selection of relevant context element, a filter may also comprise modified matching function, so that the matching function may be different for different context, e.g., user/task combinations. For example, a filter may select or dis-select a 'patient age'-element from the context, but may also modify the weighing of 'patient age' in the matching function.

If a document has multiple tags, the match valuation may be increased if more than one of the multiple tags match second context 242.

For example, consider a radiologist who selects a document containing skeletal age norms supporting his/hers current interpretation task of defining the skeletal age of a young male patient. Subsequently, a colleague radiologist who is performing the task of determining the skeletal age of another young male patient, via study description and age information, will be assisted by the system by document proposals containing the document with norms on skeletal age.

The system may be improved by recording if a suggested document was not actually selected. The system thus learns that a given document is not relevant in the current document. If many of these events are recorded the system may remove tags from the document, to avoid its suggestion.

The system may also be improved by ordering suggested documents according to match valuation.

Typically, the device 150 and the 250 each comprise a microprocessor (not shown) which executes appropriate software stored at the device 150 and the 250; for example, that software may have been downloaded and/or stored in a corresponding memory, e.g., a volatile memory such as RAM or a non-volatile memory such as Flash (not shown). Alternatively, the devices 150 and 250 may, wholly or partially, be implemented in programmable logic, e.g., as field-programmable gate array (FPGA).

One embodiment of document requesting unit 150 and document suggestion unit 250 is as follows. Information is constantly collected on temporary context storage 140, sometimes referred to as the 'blackboard', e.g. via add-ons to existing applications. The information may include: Patient context: e.g. exam information such as an exam description; User information: expertise and Task information: request. The information on temporary context storage 140 may be semantically normalized by encoding the information in through a concept list. For example, the exam description may be mapped to one or more body region codes.

When a document is selected a script starts, e.g. via an agent. Selection of a document may be detected by a trigger that triggers that a document has been open for more than some threshold seconds, say 7 seconds. This filters out accidental or unrelated openings of documents.

The script tags the document with the information in temporary context storage 140. The script may also collect which parts of the document are visited, e.g., page, or section.

Figure 3A:
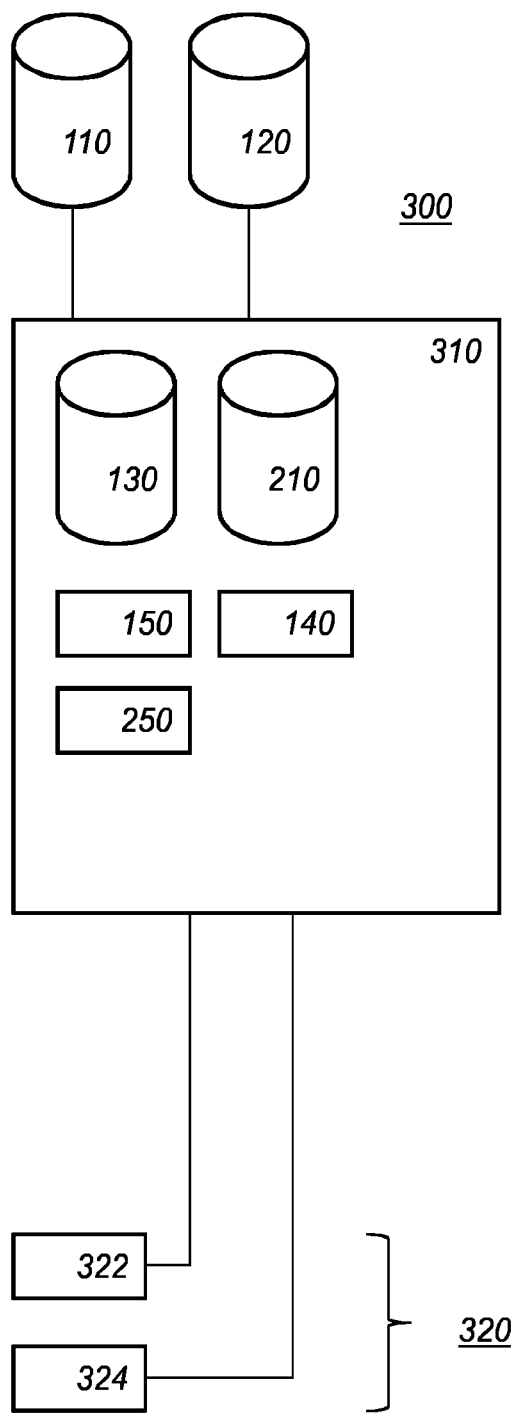
FIG. 3a is schematic block diagram of a document management system 300.
Figure 3B:
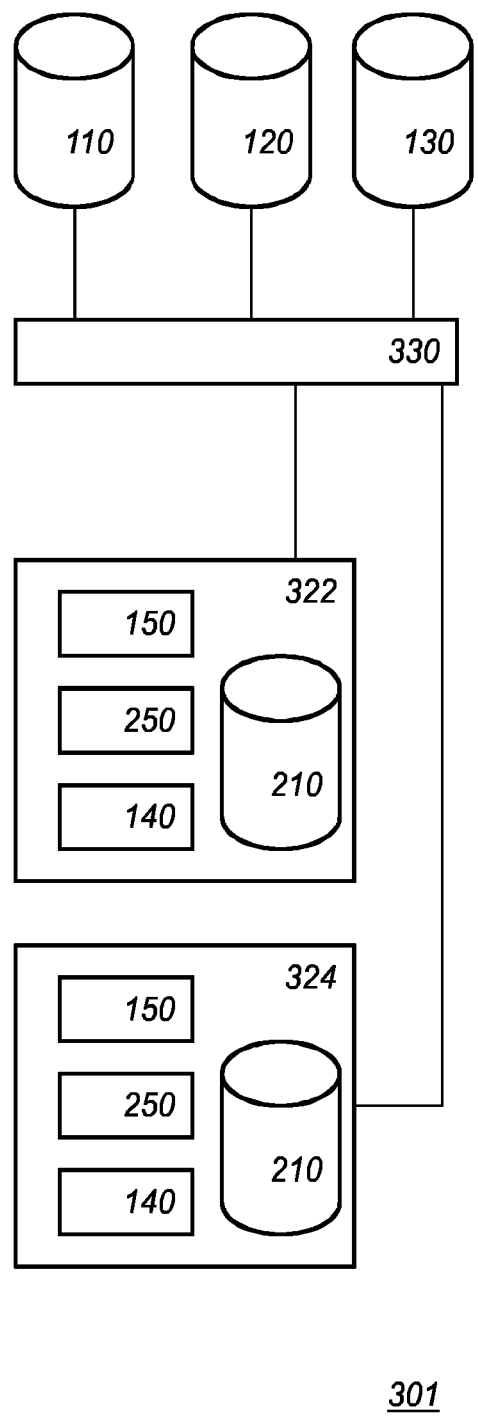
FIG. 3b is schematic block diagram of a document management system 301.

FIGS. 3*a* and 3*b* show to different ways to integrate document requesting unit 150 and document suggestion unit 250 into a larger system.

FIG. 3*a* shows a server 310, which may be part of a hospital information system, comprising document requesting unit 150, and document suggestion unit 250. Optionally, server 310 uses a tag database 130 to keep tags, a temporary context storage 140 to temporarily store context and a filter database 210 to store filters. Server 310 is connected with patient database 110 and document database 120, the latter could also be part of document requesting unit 150 but this is not necessary and often inconvenient. Multiple users 320 can use server 310 using their own computing device connected to server 310 over a computer network, say a LAN, internet a Wi-Fi network, and the like. The computing devices in FIG. 3*a* need relatively little computing power, and may be a computer terminal running a browser, a tablet etc.

Note that multiple users add tags to documents using document requesting unit 150, which means that a user may receive suggested documents based on documents that were earlier requested and tagged by another user.

FIG. 3*b* shows system 301, which is an alternative to the system 300. In system 301 users 320 access different workstations 322 and 324. Each workstation contains an document requesting unit 150, document suggestion unit 250, and optionally temporary context storage 140 and/or filter database 210. The workstations have access to patient database 110, document database 120 and tag database 130 and may modify the latter. In this case access goes through a common interface 330, but this is not necessary.

As in system 300, requests of one user may set tags that cause a suggestion to a second user. Interestingly, system 301 may also contain one or more workstations (not shown) that do not contain a document requesting unit 150. Such a workstation cannot cause tag to be set, but can profit from the tags set by others. For example, such a workstation may be suitable for student users.

Figure 4:
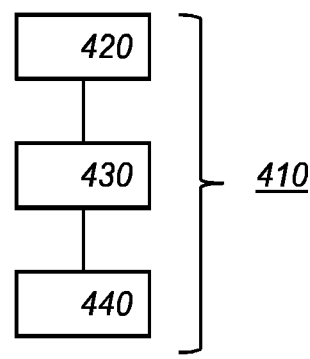
FIG. 4 is a schematic flowchart of a document management method 400.

FIG. 4 is a schematic flowchart of a document management method 400 comprising a document query method 410 for retrieving documents to assist a user in a first clinical task on patient data of a first patient. The document requesting method comprises:

determining a first context 420 based on the first clinical task and/or the patient data of the first patient, retrieve a document 430 selected by the user from an electronic document database 120, and tagging 440 the selected document with the first context to enable a document suggestion method to suggest the selected document during a second clinical task on patient data of a second patient.

Figure 5:
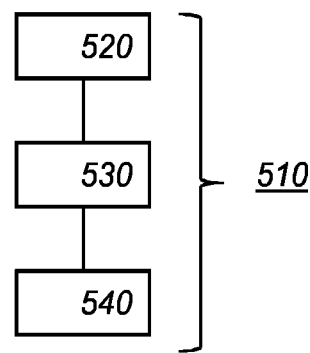
FIG. 5 is schematic flowchart of a document suggestion method 510, FIG. 6 schematically shows an exemplary embodiment of the workstation 600.

FIG. 5 is schematic flowchart of a document suggestion method 510 for suggesting a document to the user to assist the user in the second clinical task on patient data of the second patient. Document suggestion method 510 may be part of document management method 400, e.g., follow document query method 410. Document suggestion method 510 comprises:

determining 520 a second context 242 based on the second clinical task and/or the patient data of the second patient, determining 530 a match valuation between the second context and a tagged context of a candidate document 222 in the document database (120), and suggesting 540 the candidate document to the user if the match valuation is high according to a suggestion function.

Method 410 may be repeated as often as needed, to request and tag multiple documents by one or multiple users. Method 510 may be used by users that may or may not have tagged documents themselves.

Many different ways of executing the method are possible, as will be apparent to a person skilled in the art. For example, the order of the steps can be varied or some steps may be executed in parallel. Moreover, in between steps other method steps may be inserted. The inserted steps may represent refinements of the method such as described herein, or may be unrelated to the method. For example, methods 410 and 510 may be executed, at least partially, in parallel. Moreover, a given step may not have finished completely before a next step is started.

A method according to the invention may be executed using software, which comprises instructions for causing a processor system to perform method 400 and/or 500. Software may only include those steps taken by a particular sub-entity of the system. The software may be stored in a suitable storage medium, such as a hard disk, a floppy, a memory etc. The software may be sent as a signal along a wire, or wireless, or using a data network, e.g., the Internet. The software may be made available for download and/or for remote usage on a server. A method according to the invention may be executed using a bitstream arranged to configure programmable logic, e.g., a field-programmable gate array (FPGA), to perform a method according to the invention.

Figure 6:
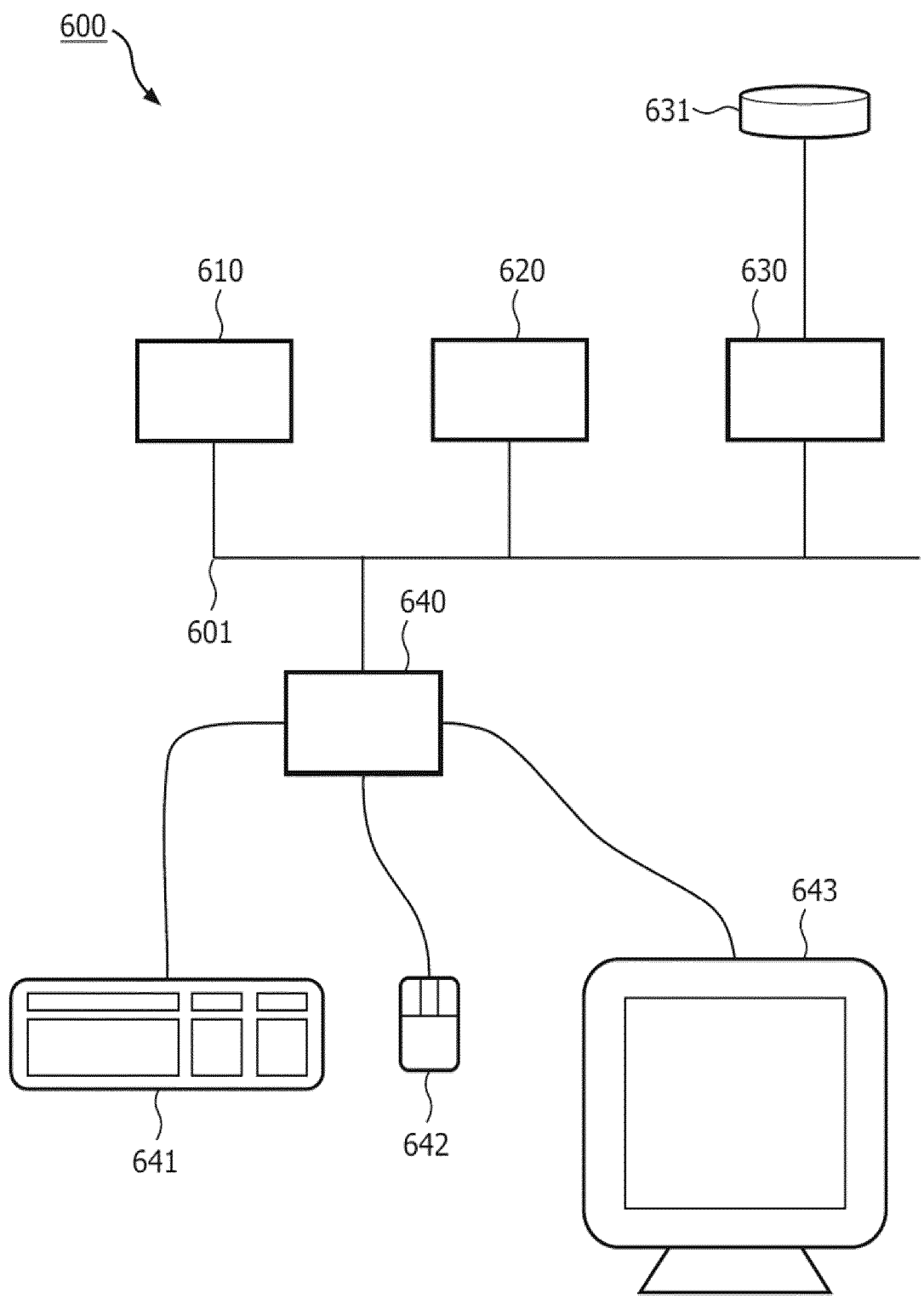

FIG. 6 schematically shows an exemplary embodiment of the workstation 600. The workstation comprises a system bus 601. A processor 610, a memory 620, a disk input/output (I/O) adapter 630, and a user interface (UI) 640 are operatively connected to the system bus 601. A disk storage device 631 is operatively coupled to the disk I/O adapter 630. A keyboard 641, a mouse 642, and a display 643 are operatively coupled to the UI 640. The system 100 of the invention, implemented as a computer program, is stored in the disk storage device 631. The workstation 600 is arranged to load the program and input data into memory 620 and execute the program on the processor 610. The user can input information to the workstation 600, using the keyboard 641 and/or the mouse 642. The workstation is arranged to output information to the display device 643 and/or to the disk 631. A person skilled in the art will understand that there are numerous other embodiments of the workstation 600 known in the art and that the present embodiment serves the purpose of illustrating the invention and must not be interpreted as limiting the invention to this particular embodiment.

Receiving input from the user may use a variety of input means, including, touch screen, mouse, keyboard, and the like. Workstation 600 may be used to implement the workstations of FIG. 3b, but also the computing devices of FIG. 3a, and server 310.

Figure 7:
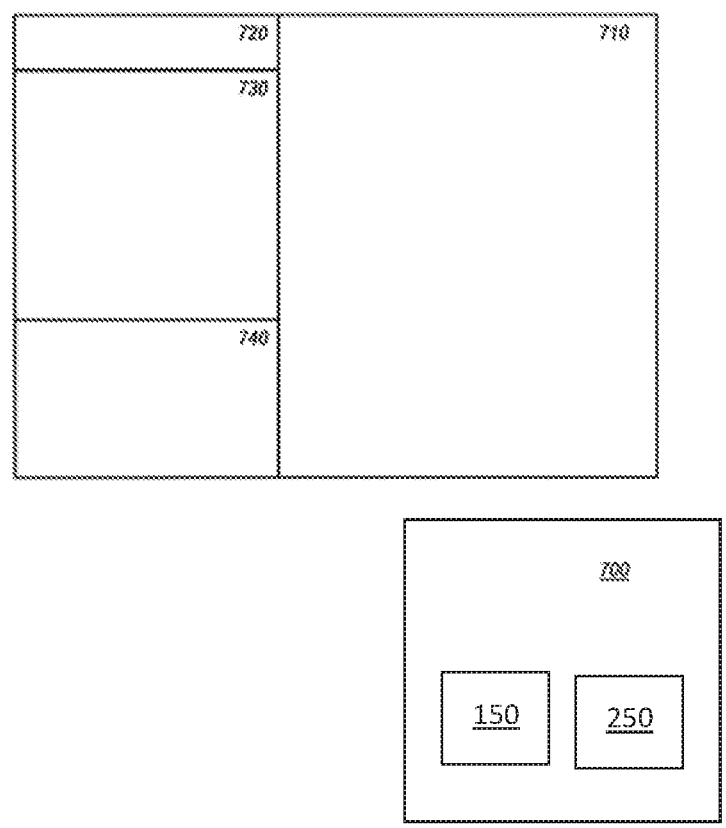
FIG. 7 is a schematic representation of screenshot 700 of device having a document requesting unit 150 and document suggestion unit 250.

FIG. 7 is a schematic representation of screenshot 700 of device having an document requesting unit 150 and document suggestion unit 250. This screenshot is one possibility of many, although this choice proved advantageous with users. A part of the screenshot 700, in this case patient data part 710, shows patient data, a different part of screenshot 700 shows document data, in this case parts 720, 730 and 740.

Patient data part 710 shows the patient data the current task is concerned with, for example, it may show an image for evaluation, say, an x-ray image or the like.

Part 740 is a file browser, allowing the user to manually select a document from a file hierarchy, e.g., a directory structure. Part 720 is an input box for entering a query. Part 730 has a dual use. After a user entered a query in part 720, then part 730 shows the responding documents, possibly sorted by a sorting unit 154. If no query has been entered, part 730 shows one or more suggested documents.

In a learning phase, a user selects a document during the interpretation of a medical case. The document is tagged with, say, a combination of user, task and patient information. In an execution phase, while in the context of a current user, medical task, patient case, automatically a list of documents is compiled that were used by the current user or a colleague in executing a comparable task for a comparable patient study.

Figure 8:
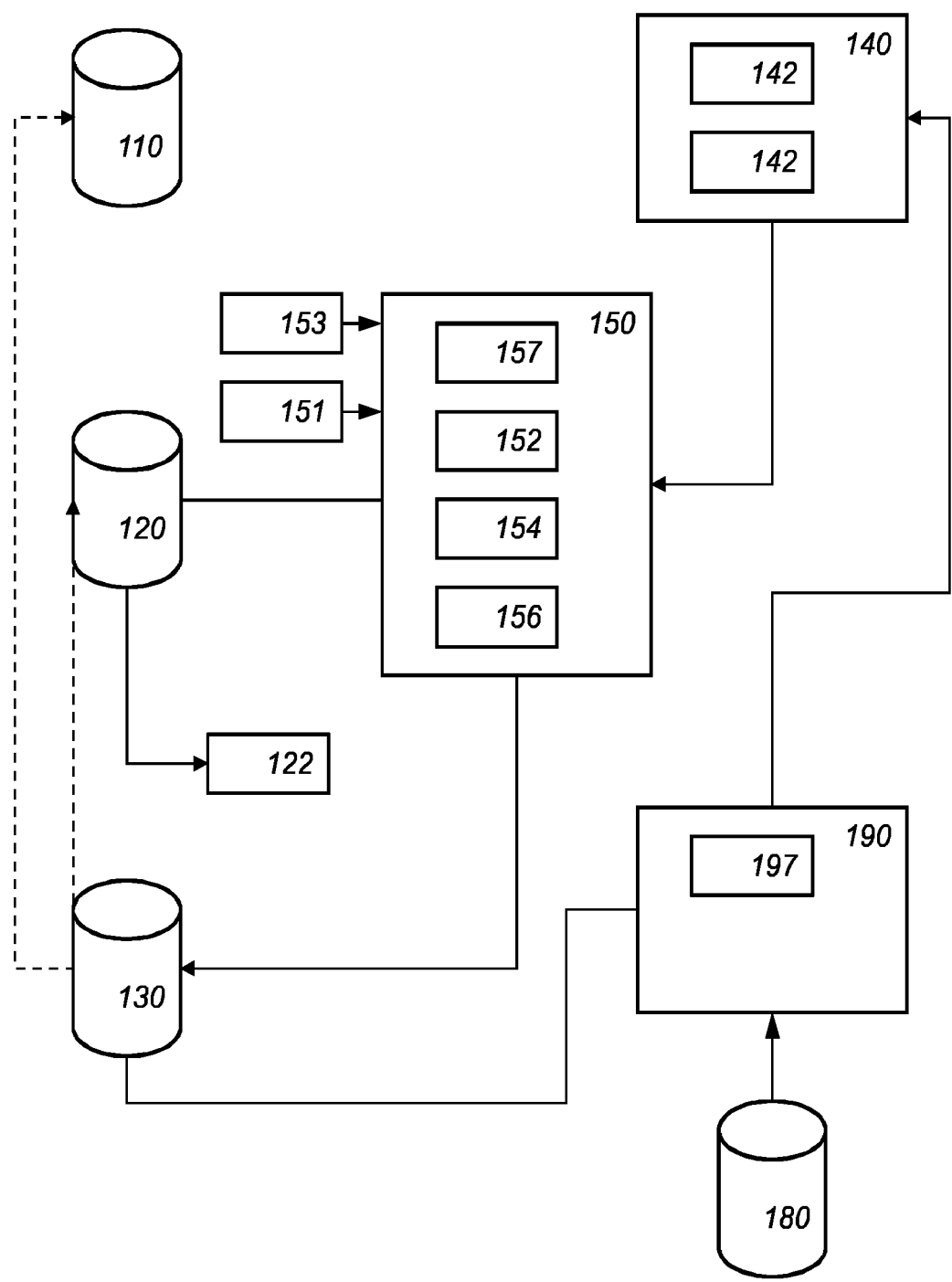
FIG. 8 is schematic block diagram of a document management system 101.

FIG. 8 is schematic block diagram of a document management system 101.

It would be advantageous to have a further improved document management system that is able to suggest documents based on information that was not available during the usage of a document. For example, it would be advantageous to have a system supporting the task of finding a document via a decision that was made after using a document.

An enhanced document management system containing document tag completion unit is proposed that is arranged to amend a context according to a tag completion database that describes which context elements are available in the future to clinically meaningful enrich a certain first situational context with experience, containing at least a conclusion for a certain occasion and a result for a certain occasion and conclusion. This has the advantage that the document management system can suggest documents that were used in comparable occasions, comparable conclusions and comparable results or a combination thereof.

Shown in FIG. 8 is a tag completion unit 190, a context builder 197, and a tag completion database 180. Document requesting unit 150 is configured for retrieving documents to assist a user in a clinical task on patient data of a patient. The document requesting unit 150 comprises a database access unit 152. The database access unit is configured to retrieve a document 122 selected by the user from an electronic knowledge source database 120. Database 120 contains a definition of a hospital's trusted sources.

The document requesting unit contains a context builder 157 is configured to determine a first context 142 based on a description of the first clinical task and/or the patient data of the first patient. Informally, the context builder 157 builds an electronic representation of the context in which selected document 122 was requested.

Document requesting unit 150 comprises a tagging unit 156 configured to tag the selected document 122 with the first context to enable a document suggestion unit 250 to suggest the selected document 122 during a second clinical task on patient data of a second patient. Document suggestion unit 250 may be part of system 101.

Access to document database 120 may be implemented in several ways. For example, document requesting unit 150 may offer a file browser. Through the file browser the user can select the file he requests. For example, document requesting unit 150 may show a list of document names or a document tree, say organized by topic, from which a document may be selected.

In an embodiment, document management system 101 comprises an electronic tag database 130, wherein the tagging unit 156 is configured to tag the selected document 122 by recording in the tag database 130 the first context together with a reference to the selected document 122 in the document database 120. Storing tags in a separate database avoids the need to modify document database 120; this is suited for external databases.

Information not available at the time of tagging the document and related to the document may be stored in database 130.

The document requesting unit may contain a tag completion unit 190 configured to extend a specific tag based on a description of which items to add to a tag based on information in a tag completion database. The tag completion database describes which tags may be obtained based on other tags already present. It may as well contain rules to conditionally extend a tag based on the value of a context element. For example, the patient information may include information describing the physical condition of the patient, e.g., age, gender, existing conditions, lifestyle information, e.g., smoking or non-smoking. In addition a time stamp might be added when the context was added. In case of a specific age range, additional patient information might be obtained.

In another embodiment, the tag database may also contain rules to delete a tag. For example if a document was closed within an interval defined by a threshold it might be concluded that the document was not used at all.

The tag completion unit 190 contains a context builder 197 and is configured to determine a context 143 based on a description of the required item in the tag completion database. Informally, the context builder 197 builds an electronic representation of the context after the selected document 122 was requested as defined by the tag completion database.

It would be advantageous to have an improved document management system that is able to suggest documents based on user preferences and experience that was not available during the previous use of a document. For example, it would be advantageous to have a system supporting the task of finding a document via a decision that was made after using a document. Furthermore, it would be advantageous to have an improved document management system that would be able to show decisions based on usage of the identical document in context of comparable occasions.

Document tag completion unit 190 may be arranged to amend a context tag according to a tag completion database that describes which context elements, available in the future, clinically meaningful enrich a certain first situational context with experience, containing at least a conclusion for a certain occasion and a result for a certain occasion and conclusion. The tag completion unit may constantly monitor context changes after first usage of a document to enrich the document.

This enables the document management system to find documents based on information obtained in a later phase (e.g. propose documents on comparable decisions after having consulted a knowledge source). Furthermore it enables to browse through medical experience grouped via used knowledge sources. In other words, a system is proposed that will enrich reference materials with experience data based on actual usage of the documents, such that the system can propose documents based on experience rather than situational knowledge only. The documents in a sense automatically group the medical information: (e.g. occasion, decision, and outcome).

The document requesting unit may comprise a context builder unit. The context builder is configured to determine a context based on the case data of the current patient. Furthermore, the document requesting unit is configured to tag a document with the current context. The document management system comprises a tag completion unit configured to extend the tag based on information stored in a tag completion database. An element in the tag completion unit describes which additional elements need to be gathered based on the initial context.

For example, based on the initial tag (context elements describing the occasion e.g. study description), the second section is described by context elements describing the conclusion (the medical report) and a third section is described by context elements describing the result (e.g. therapy response). The tag completion unit will continue gathering information automatically after a clinical user focuses on a next patient case.

Figure 9:
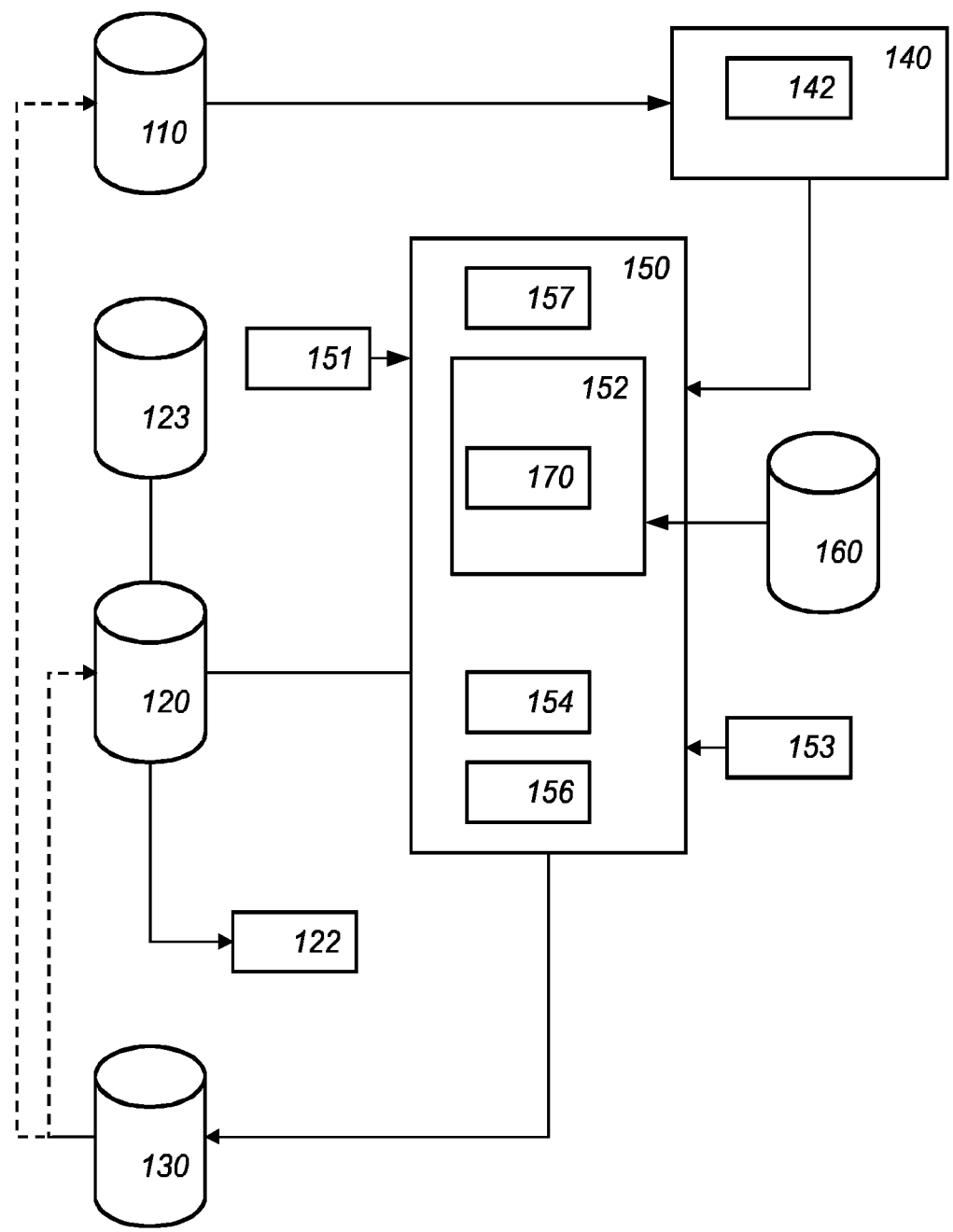
FIG. 9 is schematic block diagram of a document management system 102.

FIG. 9 is schematic block diagram of a document management system 102.

As significant amounts of information have to be analyzed by clinicians to make informed decisions, it would be advantageous to have a system that assists in a unified access to sources as well as a system that avoids unintended identification of a patient. A document management system is proposed that is arranged to create query commands automatically, based on user queries, for sources that comprise the document database such that patient information allowing identification of a patient is only shared with appropriate parts of the document management system, and not shared with e.g. third parties. As a consequence, patient information is used better to obtain search results.

The document database of a document management system may be a collection of a hospital's trusted sources, i.e., a collection of documents that the hospital wants its professionals to work with. Sources in the document database may also be obtained as a subscription service from an external document provider. In effect, the document database may be comprised of several sub-databases. For example, document database may contain one or more of: Scientific literature, Guidelines, Clinical trials, Hospital trusted sources, and User's trusted sources including the patient records.

The document management system may hide the source to users, unifying the access to documents. When clinicians create queries to retrieve information supporting a clinical task on a patient, information might be shared via queries to external parties that could be used to identify a patient. In a clinical environment it would be advantageous if patient information is not used unintended. It would be advantageous to have an improved document management system that avoids information to be spread to external parties, allowing an unintended identification of a patient.

A document management system is proposed that comprises a document requesting unit for retrieving documents, wherein the document management system is comprised of one or more sub-databases with source definitions, wherein the document requesting unit is arranged to create query commands automatically, based on user queries such that patient information allowing identification of a patient is only shared with appropriate parts of the document management system, and not shared with e.g. third parties.

To accomplish this, the document requesting unit comprises a context unit. The context builder is configured to determine a context based on the case data of the current patient. Furthermore, the requesting unit is arranged to create query commands based on the user query and filtered using the context elements stored in a db containing filter rules or access rules for the sub-databases that compose the knowledge source database. As a consequence, patient information is optimally used to obtain search results internally while automatically hiding the information when de-identification is required for external sources. Composing the specific query for a sub database to avoid information being spread that allows unintended identification of a patient avoids this problem.

Shown in FIG. 9 is a query filter 170, sub-database access rules 160, and a sub-database 123. Document management system 102 is arranged to approach sub-databases 123 that describe the knowledge database 120 with de-identified queries based on rules defined per sub-database 160, patient context 140 and a user provided query 151. The resulting system allows unified access to sources optimally using patient information when appropriate to allow the user to select a document 122 from a result set provided by the system.

A document requesting unit 150 is configured for retrieving documents to assist a user in a clinical task on patient data of a patient. The document requesting unit 150 comprises a database access unit 152. The database access unit is configured to retrieve a document 122 selected by the user from an electronic knowledge source database 120. Database 120 contains a definition of a hospital's trusted sources. Document database 120 may be comprised of several sub-databases 123 (e.g. a sub database with a collection of internal documents, and a sub database with a subscription service from a document provider).

The document requesting unit contains a context builder 157 that is configured to determine a context 142 based on a description of the patient data of a current patient. Informally, the context builder 157 builds an electronic representation of the context in which a document is requested. The patient information may include information describing the physical condition of the patient, e.g., age, gender, birth date, existing conditions, lifestyle information, e.g., smoking or non-smoking obtained from the patient database 110. The patient database may be part of a hospital information system.

Document requesting unit 150 is suited for use with a query based document request system. The database access unit 152 may be configured to receive a query 151 from the user. Database unit 152 is configured to determine responding documents from document database 120.

To accomplish this, database unit 152 generates a command for a query for each document sub-database 123 corresponding to query 151 based on a de-identification rule database 160 that contains rules defined for each sub-database and context 142. One rule contains a definition of the patient context element from 142 that is not allowed as part of the query for a specific sub-database. For example the patients' birth date or patients' name. When part of the query matches the patient context element (e.g. patient name) it is removed from the query.

Below, a particular embodiment of a query filter unit 170 as part of the database access unit 152 is given. For example consider a match valuation between the current query "Joh" and the patient name "John". A specific rule in 160 may define that the patient name should not be in the specific query to the corresponding sub database 123. For example, if the similarity according to an 'edit distance' is above a user defined threshold (e.g. 80%), the match will be successful and the matching part "Joh" will be removed from the query.

The responding documents composed of responding documents of all sub-databases, or part thereof, are shown to the user, say as a list of document names, possibly together with a content indication. Database unit 152 is configured to receive a selection 153 from the user for one of the responding documents; in this case selected document 122.

Furthermore, in an embodiment, the de-identification of a query may as well apply to automatically created queries to allow the system to propose documents that support the current task of a clinical user.

For example, system 102 may be arranged to query a generic search engine, say Google. This search engine may be added to the document management system. In addition, an internal document containing a patient name of a patient in the hospital information system is added to the document management system. When querying the system with the patient name of a current selected patient, the internal document should be found, while the generic site will not receive the patient name query.

It will be appreciated that the invention also extends to computer programs, particularly computer programs on or in a carrier, adapted for putting the invention into practice. The program may be in the form of source code, object code, a code intermediate source and object code such as partially compiled form, or in any other form suitable for use in the implementation of the method according to the invention. An embodiment relating to a computer program product comprises computer executable instructions corresponding to each of the processing steps of at least one of the methods set forth. These instructions may be subdivided into subroutines and/or be stored in one or more files that may be linked statically or dynamically. Another embodiment relating to a computer program product comprises computer executable instructions corresponding to each of the means of at least one of the systems and/or products set forth.

It should be noted that the above-mentioned embodiments illustrate rather than limit the invention, and that those skilled in the art will be able to design many alternative embodiments.

In the claims, any reference signs placed between parentheses shall not be construed as limiting the claim. Use of the verb "comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention claimed is:

1. A document management system, comprising at least one processor programmed to retrieve documents to assist a first user in a first clinical task on patient data of a first patient, the at least one processor being configured to:
    determine a first context based on a description of the first clinical task and/or the patient data of the first patient;
    retrieve a document selected by the first user from an electronic document database;
    tag the selected document with the first context to enable a suggestion of the selected document during a second clinical task on a second patient by a second user;
    suggest a document to the second user to assist the second user in the second clinical task on patient data of the second patient by operations including:
        determining a second context based on the second clinical task and/or the patient data of the second patient, and
        determining a match valuation between the second context and a tagged context of a candidate document in the document database and to suggest the candidate document to the second user if the match valuation is high according to a suggestion function;
    wherein the first context and the second context both include information related to a seniority of a corresponding one of the first user and the second user,
    the at least one processor is configured to determine a match valuation between the seniority of the first user and the seniority of the second user, wherein the seniority of the second context does not match a tag with a lower seniority level of the first context; the match valuation including, when the seniority of the second user is higher than the seniority of the first user, then the first and second users are not matched, and when the seniority of the second user is lower than the seniority of the first user, then the first and second users are matched;
    wherein the at least one processor is configured to receive a user query from the first user, to determine responding documents from the electronic document database, and to receive a selection from the first user for said selected document of the responding documents;
    wherein the document management system further includes an access rules database comprising access rules for sub-databases, wherein the access rules of the access rules database indicate forbidden context elements in queries to the sub-databases;
    the at least one processor is configured to generate multiple query commands corresponding to the user query for each of multiple sub-databases respectively;
    the system comprising a query filter arranged to remove a particular query for a particular sub-database from the multiple query commands if the particular query comprises a context element from first context which may not occur in a query to the particular sub-database according to an access rule of the access rules database, and
    the at least one processor is configured to execute the multiple query commands after filtering by the query filter.

2. The document management system as claim 1, wherein the at least one processor is further configured to base a context additionally on at least one of:
    identity information of the user, and
    a role of the user.

3. The document management system as in claim 1, wherein the at least one processor is further configured to include a reference to the patient data in the electronic patient database.

4. The document management system as in claim 1, comprising an electronic tag database, wherein the at least one processor is configured to tag the selected document by recording in the tag database the first context together with a reference to the selected document in the electronic document database.

5. The document management system as in claim 1, wherein the at least one processor is configured to sort the responding documents according to suitability, wherein the suitability of a particular document is determined by matching a tag of the particular document with the first context.

6. The document management system as in claim 1, wherein the at least one processor includes a context filter, the context filter selecting part of the information from the second context according to a filter associated with the user and/or second task, and
    the at least one processor is configured to determine a match valuation between the selected part of the second context and a tagged context of a candidate document in the electronic document database.

7. The document management system as in claim 1, wherein the at least one processor is configured to correlate the second context with a tagged context of a candidate document to obtain the match valuation.

8. The document management system as in claim 1, wherein the at least one processor includes a concept list and is configured to map at least part of the second context to one or more concepts of the concept list and to determine a correlation between the one or more concepts and a tag of the candidate document to obtain the match valuation.

9. The document management system as in claim 1 comprising a tag completion database,
    the tag completion database describing which context elements may extent a first context, and
    the at least one processor is configured to monitor case data of the first patient for context elements described in the tag completion database, and to extent the first context upon finding said context elements.

10. The document management system of claim 1, wherein the seniority is indicative of a number of years of experience of the user.

11. A document management workstation, comprising at least one computer processor programmed to:
    determine a first context based on a description of a first clinical task and/or patient data of a first patient;
    retrieve a document selected by a first user from an electronic document database;
    tag the selected document with the first context;
    store, in the electronic document database, the selected document as a candidate document tagged with the first context;
    determine a second context based on a second clinical task and/or patient data of a second patient;
    determine a match valuation between the second context and the first context of the candidate document; and in response to the match valuation being exceeding a threshold according to a suggestion function, controlling a user interface to suggest the candidate document to the second user;

wherein the first context and the second context both include information related to a seniority of a corresponding one of the first user and the second user, and the at least one computer processor is configured to determine a match valuation between the seniority of the first user and the seniority of the second user, wherein the seniority of the second context does not match a tag with a lower seniority level of the first context, the match valuation including, when the seniority of the second user is higher than the seniority of the first user, then the first and second users are not matched, and when the seniority of the second user is lower than the seniority of the first user, then the first and second users are matched;

wherein the at least one processor is configured to receive a user query from the first user, to determine responding documents from the electronic document database, and to receive a selection from the first user for said selected document of the responding documents;

wherein the document management system further includes an access rules database comprising access rules for sub-databases, the access rules of the access rules database indicating forbidden context elements in queries to the sub-databases;

the at least one processor is configured to generate multiple query commands corresponding to the user query for each of multiple sub-databases respectively;

the system comprising a query filter arranged to remove a particular query for a particular sub-database from the multiple query commands if the particular query comprises a context element from first context which may not occur in a query to the particular sub-database according to an access rule of the access rules database, and the at least one processor is configured to execute the multiple query command after filtering by the query filter.

12. The document management workstation as in claim 11, wherein the at least one computer processor is programmed to:

utilize a context filter to select a portion of information from the second context according to a different filter associated with the user and/or second task; and determine a match valuation between the selected part of the second context and a tagged context of a candidate document in the electronic document database.

13. The document management workstation as in claim 11, wherein the at least one computer processor is programmed to:

correlate the second context with a tagged context of a candidate document to obtain the match valuation.

14. The document management workstation as in claim 11, wherein the at least one computer processor is programmed to:

map at least part of the second context to one or more concepts of a concept list; and determine a correlation between the one or more concepts and a tag of the candidate document to obtain the match valuation.

15. The document management system of claim 11, wherein the seniority is indicative of a number of years of experience of the user.

* * * * *